US012797867B2

(12) United States Patent
Weber et al.

(10) Patent No.: US 12,797,867 B2
(45) Date of Patent: Nov. 17, 2026

(54) CENTRIFUGE WITH CONTACTLESS POWER SOURCE FOR ACTIVE ELECTRONIC DEVICE

(71) Applicant: Fenwal, Inc., Lake Zurich, IL (US)

(72) Inventors: Mark C. Weber, Round Lake Beach, IL (US); Mark Ern, Buffalo Grove, IL (US); Michael J. Kast, Crystal Lake, IL (US); James C. Han, Crystal Lake, IL (US)

(73) Assignee: Fenwal, Inc., Lake Zurich, IL (US)

(*) Notice: Subject to any disclaimer, the term of this patent is extended or adjusted under 35 U.S.C. 154(b) by 667 days.

(21) Appl. No.: 18/183,662

(22) Filed: Mar. 14, 2023

(65) Prior Publication Data

US 2023/0294111 A1 Sep. 21, 2023

Related U.S. Application Data

(60) Provisional application No. 63/320,898, filed on Mar. 17, 2022.

(51) Int. Cl.

| | |
|---|---|
| ***B01L 3/00*** | (2006.01) |
| ***A61M 1/36*** | (2006.01) |
| ***B01D 15/08*** | (2006.01) |
| ***B01F 33/302*** | (2022.01) |
| ***B01F 33/3033*** | (2022.01) |
| ***B01J 8/00*** | (2006.01) |
| ***B01J 8/02*** | (2006.01) |
| ***B01J 20/285*** | (2006.01) |

(Continued)

(52) U.S. Cl.

CPC ............. *B04B 5/10* (2013.01); *A61M 1/3693* (2013.01); *B04B 7/08* (2013.01); *H02J 50/005* (2020.01); *B04B 2013/006* (2013.01)

(58) Field of Classification Search

CPC ....... B04B 5/10; B04B 7/08; B04B 2013/006; B04B 5/04; B04B 13/00; A61M 1/3693; A61M 2205/331; A61M 1/3609; A61M 2205/3561; A61M 2205/3569; A61M 2205/3584; A61M 2205/8243; A61M 2209/086; H02J 50/005

See application file for complete search history.

(56) References Cited

U.S. PATENT DOCUMENTS 5,525,218 A * 6/1996 Williamson, IV .... B04B 5/0442 210/512.1

6,254,784 B1 7/2001 Nayak (Continued)

FOREIGN PATENT DOCUMENTS

JP 2005536293 A 12/2005

JP 2022549202 A 11/2022

(Continued)

OTHER PUBLICATIONS

Extended European Search Report for European Patent Application No. 23161710.1, Mailed Jul. 19, 2023.

(Continued)

*Primary Examiner* — Oyeleye Alexander Alabi

(74) *Attorney, Agent, or Firm* — Cook Alex Ltd.

(57) ABSTRACT

A centrifuge assembly including a rotating component and an active electronic device associated with the rotating component. The active electronic device being powered by a contactless power source.

19 Claims, 5 Drawing Sheets

(51) Int. Cl.

| | |
|---|---|
| ***B01J 20/287*** | (2006.01) |
| ***B01J 20/32*** | (2006.01) |
| ***B01L 7/00*** | (2006.01) |
| ***B01L 9/00*** | (2006.01) |
| ***B04B 5/10*** | (2006.01) |
| ***B04B 7/08*** | (2006.01) |
| ***B33Y 10/00*** | (2015.01) |
| ***B33Y 80/00*** | (2015.01) |
| ***B65G 47/80*** | (2006.01) |
| ***B82Y 20/00*** | (2011.01) |
| ***B82Y 30/00*** | (2011.01) |
| ***B82Y 40/00*** | (2011.01) |
| ***C08L 5/08*** | (2006.01) |
| ***C12M 1/34*** | (2006.01) |
| ***C12M 3/06*** | (2006.01) |
| ***C12N 1/14*** | (2026.01) |
| ***C12N 1/20*** | (2026.01) |
| ***C12Q 1/02*** | (2006.01) |
| ***C12Q 1/6806*** | (2018.01) |
| ***C12Q 1/6844*** | (2018.01) |
| ***C12Q 1/6848*** | (2018.01) |
| ***C12Q 1/6851*** | (2018.01) |
| ***C12Q 1/686*** | (2018.01) |
| ***G01K 1/14*** | (2021.01) |
| ***G01N 1/44*** | (2006.01) |
| ***G01N 15/10*** | (2024.01) |
| ***G01N 15/14*** | (2024.01) |
| ***G01N 15/1433*** | (2024.01) |
| ***G01N 21/01*** | (2006.01) |
| ***G01N 21/03*** | (2006.01) |
| ***G01N 21/05*** | (2006.01) |
| ***G01N 21/29*** | (2006.01) |
| ***G01N 21/33*** | (2006.01) |
| ***G01N 21/35*** | (2014.01) |
| ***G01N 21/59*** | (2006.01) |
| ***G01N 21/65*** | (2006.01) |
| ***G01N 21/75*** | (2006.01) |
| ***G01N 21/77*** | (2006.01) |
| ***G01N 27/07*** | (2006.01) |
| ***G01N 27/28*** | (2006.01) |
| ***G01N 27/416*** | (2006.01) |
| ***G01N 30/02*** | (2006.01) |
| ***G01N 30/60*** | (2006.01) |
| ***G01N 30/72*** | (2006.01) |
| ***G01N 31/10*** | (2006.01) |
| ***G01N 31/12*** | (2006.01) |
| ***G01N 33/543*** | (2006.01) |
| ***G01N 33/557*** | (2006.01) |
| ***G01N 33/564*** | (2006.01) |
| ***G01N 33/574*** | (2006.01) |
| ***G01N 33/575*** | (2026.01) |
| ***G01N 33/57515*** | (2026.01) |
| ***G01N 33/58*** | (2006.01) |
| ***G01N 33/68*** | (2006.01) |
| ***G01N 33/72*** | (2006.01) |
| ***G01N 35/00*** | (2006.01) |
| ***G01N 35/02*** | (2006.01) |
| ***H02J 50/00*** | (2016.01) |
| ***H05B 45/10*** | (2020.01) |
| ***H10W 90/00*** | (2026.01) |
| *B04B 13/00* | (2006.01) |

(56) References Cited

U.S. PATENT DOCUMENTS

| | | | | |
|---|---|---|---|---|
| 2008/0211614 | A1* | 9/2008 | Mecke | H01F 27/366 336/120 |
| 2012/0015794 | A1* | 1/2012 | Holmes | A61M 1/3696 494/37 |
| 2013/0190674 | A1* | 7/2013 | Case | G16H 40/67 604/6.01 |
| 2014/0234183 | A1* | 8/2014 | Kolenbrander | B01L 3/5021 422/533 |
| 2019/0120761 | A1* | 4/2019 | Koudelka | G01N 21/59 |

FOREIGN PATENT DOCUMENTS

| | | | |
|---|---|---|---|
| WO | 2003000380 | A1 | 1/2003 |
| WO | 2004018021 | A3 | 3/2004 |
| WO | 2008105972 | A1 | 9/2008 |
| WO | 2021091230 | A1 | 5/2021 |
| WO | 2021148831 | A1 | 7/2021 |

OTHER PUBLICATIONS

Kinahan David J et al: "Wireless Closed-Loop Control of Centrifugo-Pneumatic Valving Towards Large-Scale Microfluidic Process Integration", 2018 IEEE, Micro Electro Mechanical Systems (MEMS) 2018, Befast, Northern Ireland, UK, Jan. 21-25, 2018, pp. 1213-1216.

* cited by examiner

CENTRIFUGE WITH CONTACTLESS POWER SOURCE FOR ACTIVE ELECTRONIC DEVICE

CROSS-REFERENCE TO RELATED APPLICATIONS

This application claims the benefit of and priority to U.S. Provisional Patent Application Ser. No. 63/320,898, filed Mar. 17, 2022, the contents of which are incorporated by reference herein.

TECHNICAL FIELD

The invention relates to centrifugal systems and apparatus that includes a contactless power source for powering active devices on the rotating component of the centrifuge, and more particularly, for powering a sensor on a rotating component wherein the sensor has wireless data transfer capabilities.

BACKGROUND

Today people routinely process whole blood and blood components by centrifugation into its various therapeutic components, such as red blood cells, platelets, and plasma.

Conventional blood processing centrifuges use electrically conductive slip rings to provide electrical power to active devices on the rotating components of the centrifuge. Such slip rings also are used to transmit data between the active device and another device that is not located on the rotating component, such as a controller. However, the mechanical nature of slip rings can be unreliable and limits information that can be transferred.

There remains a need for reliable energy to and data exchange (send and/or receive) with active devices located on the rotating component of a centrifuge.

SUMMARY

There are several aspects of the present subject matter which may be embodied separately or together in the devices, systems, and methods described and/or claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto or later amended. For purposes of this description and claims, unless otherwise expressly indicated, "blood" is intended to include whole blood and blood components, such as concentrated red cells, plasma, platelets, and white cells, whether with or without anticoagulant or additives.

The following summary is to acquaint the reader generally with various potential aspects of the present subject matter, and is non-limiting and non-exclusive with respect to the various possible aspects or combinations of aspects. Additional aspects and features may be found in the detailed description herein and/or in the accompanying Figures.

By way of the present disclosure, a first aspect includes a centrifuge assembly for processing blood and/or components. The centrifuge assembly includes a base and a rotating component that rotates relative to the base. The assembly includes a contactless, such as a wireless, power source including a power source transmitter associated with the base and a power source receiver associated with the rotating component. The power source transmitter wirelessly transmits power to the power source receiver. An active electronic device is associated with the rotating component and operatively connected to the power source receiver. The power source receiver provides power to the active electronic device.

In another aspect, a method of processing blood and/or components with a centrifuge assembly. The method includes flowing blood and/or blood components to a rotating component of a centrifuge assembly and rotating the rotating component of the centrifuge assembly relative to a base. The method further includes powering an active electronic device associated with the rotating component using a contactless power source.

These and other aspects of the present subject matter are set forth in the following detailed description of the accompanying drawings.

DETAILED DESCRIPTION OF THE ILLUSTRATED EMBODIMENTS

Figure 2:
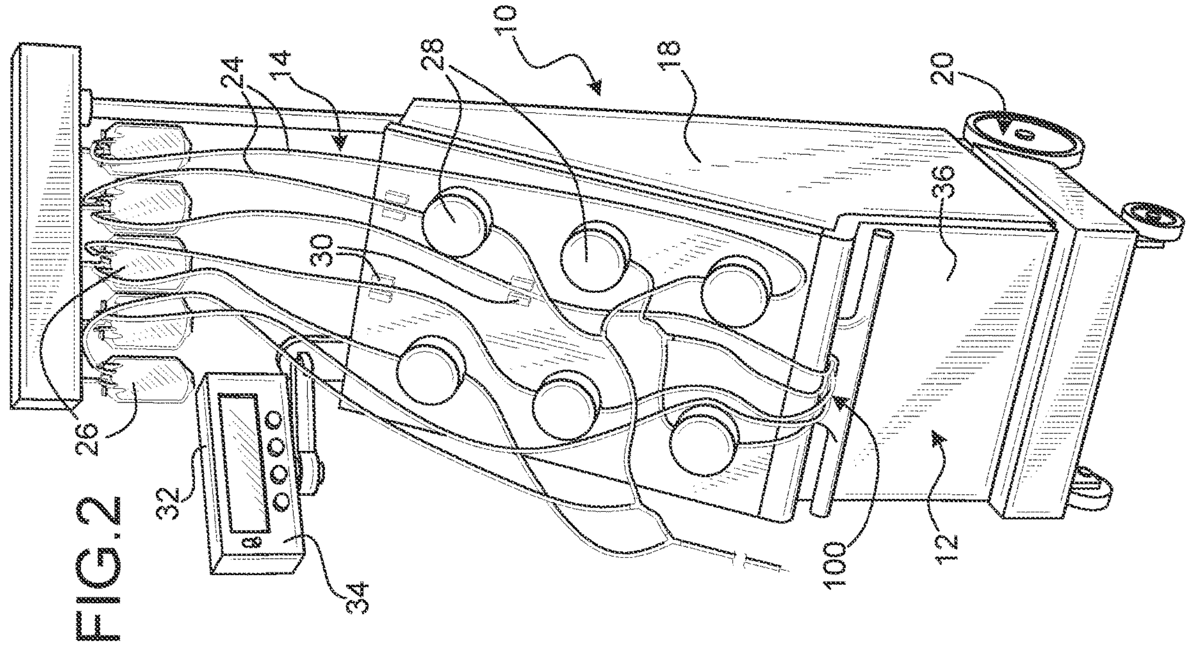
FIG. 2 is a front perspective view of the processing system shown in FIG. 1.
Figure 1:
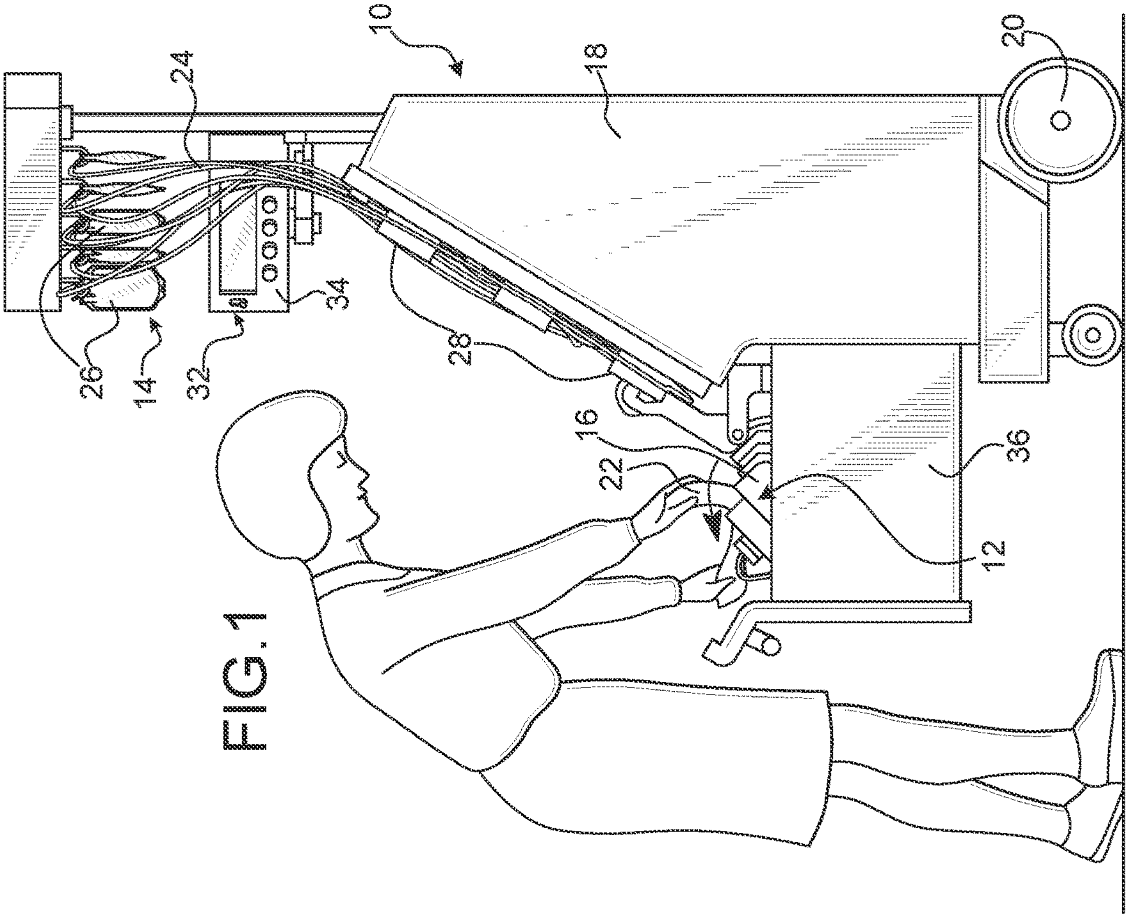
FIG. 1 is a side elevation view of an exemplary processing system that includes a centrifuge assembly in accordance with the present disclosure.

FIGS. 1 and 2 show an exemplary centrifugal processing system 10 that employs a centrifuge assembly 12 of the present disclosure. The system 10 can be used for processing various fluids. The system 10 is particularly well suited for processing whole blood and other suspensions of cellular materials that are subject to trauma.

The system 10 includes a centrifuge assembly 12 and an associated fluid processing assembly 14. The centrifuge assembly 12 is a durable equipment item. The fluid processing assembly 14 is a single use, disposable item that the user loads on the centrifuge assembly 12 before beginning a processing procedure (as FIG. 1 generally shows) and removes from the centrifuge assembly 12 upon the completing the procedure.

The centrifuge assembly 12 comprises a centrifuge 16 mounted for rotation within a cabinet 18. The user maneuvers and transports the cabinet 18 upon the associated wheels 20. It should be appreciated that, due to its compact form, the centrifuge assembly 12 also could be made as a tabletop unit.

As FIGS. 1 and 2 show, the cabinet 18 includes a sliding drawer 36 that holds the centrifuge 16. As FIG. 1 shows, the user opens the drawer 36 to access the centrifuge 16 for inserting and removing the processing chamber 22. As FIG. 2 shows, the user closes the drawer 36 when conducting a processing operation. The processing assembly 14 comprises a processing chamber 22 mounted on the centrifuge 16 for rotation (as FIG. 1 shows). An associated fluid circuit 24 conveys fluids to and from the processing chamber 22. The fluid circuit 24 has several fluid containers 26. As FIG. 2 shows, in use, the containers 26 hang from a support pole outside the cabinet 18. The fluid circuit 24 transits several peristaltic pumps 28 and clamps 30 on the face of the cabinet 18. The fluid circuit 24 enters an access opening 100 leading to the processing chamber 22 mounted within the cabinet 18. In the illustrated environment, the fluid circuit 24 preconnects the processing chamber 22 with the containers 26, forming an integral, sterile unit closed to communication with the atmosphere.

The centrifuge assembly 12 includes a processing controller 32 that coordinates the operation of the centrifuge 16. The processing controller 32 preferably uses an input/output terminal 34 to receive and display information relating to the processing procedure.

Figure 3:
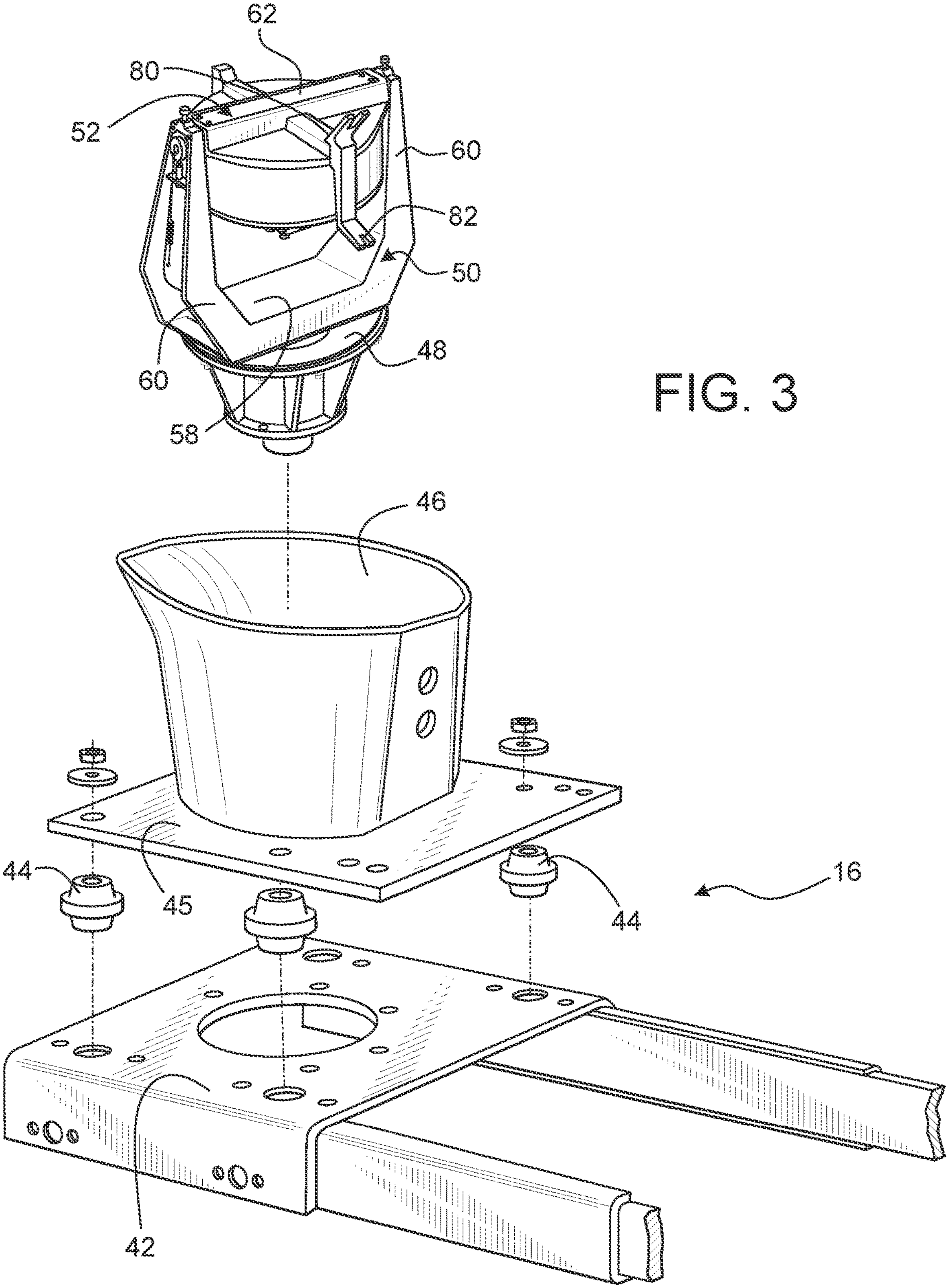
FIG. 3 is an exploded perspective view of the components of the centrifuge assembly.

As FIG. 3 shows, the centrifuge 16 includes a base 42 that supports a plate 45 mounted upon flexible isolation mounts 44. The flexible mounts 44 structurally isolate the components mounted on the plate 45 from the rest of the centrifuge 16, by dampening vibration and oscillation caused by these plate-mounted components. The components mounted on the plate 45 make up the isolated mass of the centrifuge 16.

A nonrotating outer housing or bucket 46 is mounted on the plate 45. The bucket 46 encloses a stationary platform 48, which in turn supports the rotating components of the centrifuge 16.

Figure 4:
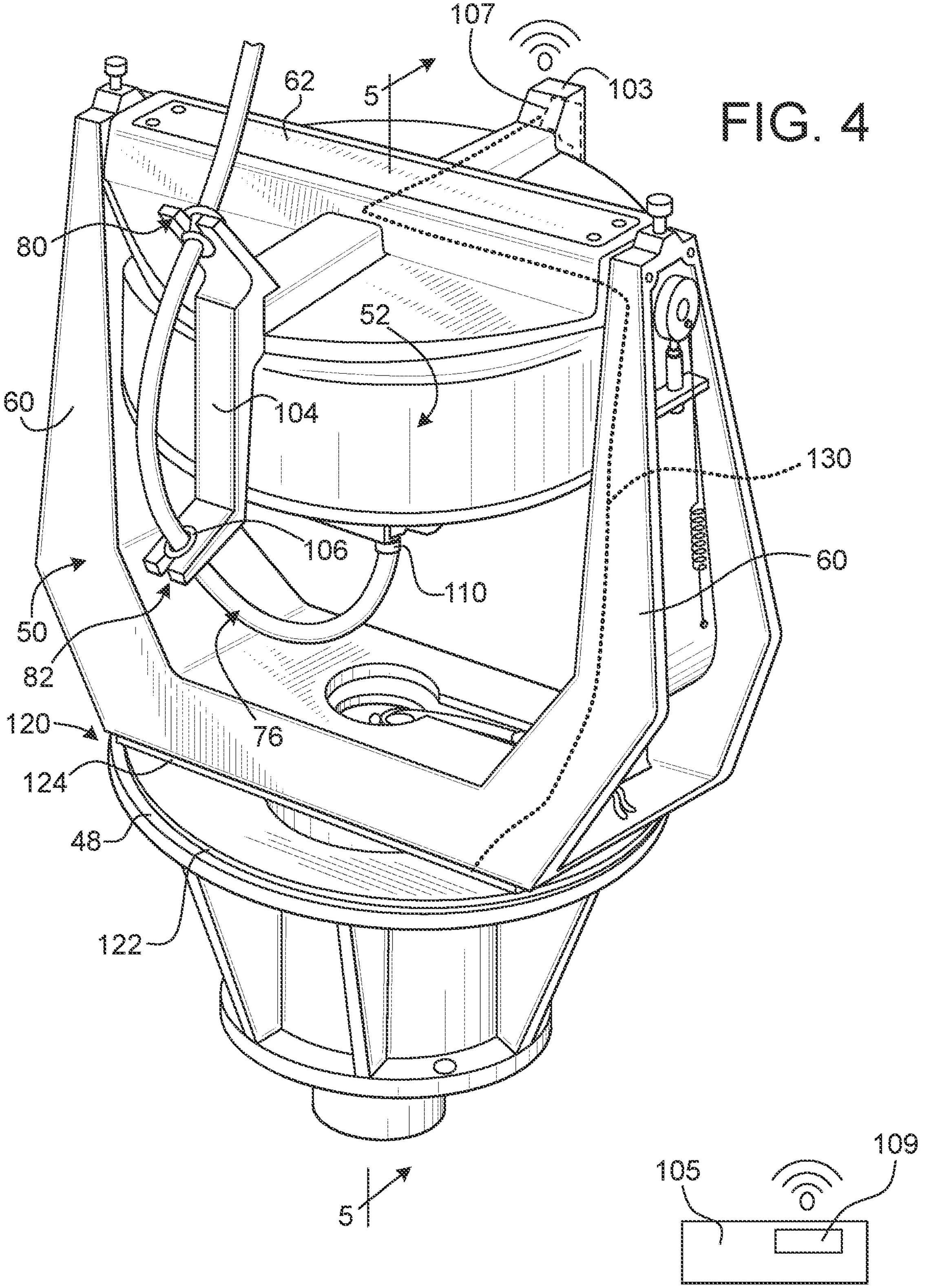
FIG. 4 is an enlarged perspective view of the rotating components of the centrifuge assembly shown in its suspended operating position.
Figure 5:
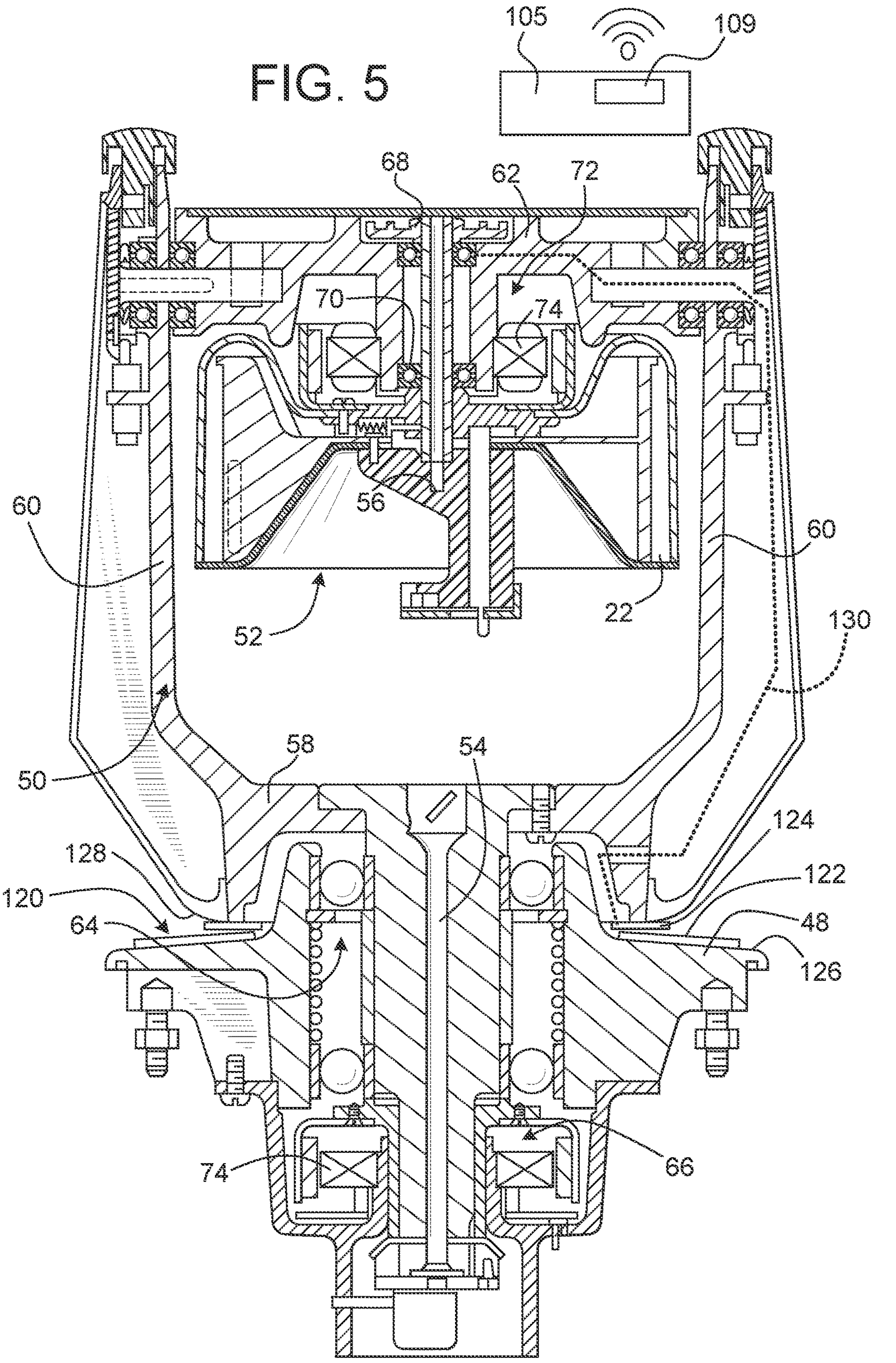
FIG. 5 is a side sectional view of the rotating components of the centrifuge assembly taken generally along line 5-5 in FIG. 4.

As FIGS. 4 and 5 show in greater detail, the rotating components include a centrifuge yoke assembly 50 and a centrifuge chamber assembly 52. The yoke assembly 50 rotates upon the platform 48 on a first drive shaft 54. The chamber assembly 52 rotates on the yoke assembly 50 on a second drive shaft 56. The rotating chamber assembly 52 carries the processing chamber 22.

The yoke assembly 50 includes a yoke base 58, a pair of upstanding yoke arms 60, and a yoke cross member 62 mounted between the arms 60. The base 58 is attached to the first drive shaft 54, which spins on a bearing element 64 about the stationary platform 48. A first electric drive 66 rotates the yoke assembly 50 on the first drive shaft 54.

The chamber assembly 52 is attached to the second drive shaft 56, which spins on a bearing element 68 in the yoke cross member 62. The second drive shaft 56 and the bearing element 68 spin as a unit on ball bearings 70. A second electric drive 72 rotates the centrifuge chamber assembly 52 on the second drive shaft.

The first electric drive 66 and the second electric drive 72 each comprises a permanent magnet, brushless DC motor. As FIG. 5 shows, the stationary platform holds the field coils 74 of the first motor 66, while the yoke base 58 comprises the armature or rotor of the first motor 66. The yoke cross member 62 holds the field coils 74 of the second motor 72, while the chamber assembly 52 comprises the associated armature or rotor.

In the illustrated embodiment, the first electric motor 66 spins the yoke assembly 50 at a predetermined speed of rotation. The second electric motor 72 spins the chamber assembly 52 at the same speed of rotation as the first electric motor 66 in the same direction and about the same axis as the spinning yoke assembly 50.

The yoke assembly 50 includes tube holders 80 and 82 that are carried by yoke cross member 62. An active electronic device 103 also is associated with the yoke 50. In the illustrated embodiment, the yoke cross member 62 carries active electronic device 103, such as a sensor that senses or measures a characteristic of the fluid being processed and/or the centrifuge. In one alternative, the active electronic device 103 may be a blood component detector, which sensors or detects various blood components and/or their interfaces. In another alternative, the active electronic device 103 may be one or more of an interface detector, pressure sensor, temperature sensor, hemolysis sensor, a weight scale or any other suitable electronic device or sensor. In another alternative the active electronic device 103 may include an optical sensor or a camera used to sense or determine characteristics of blood within the centrifuge.

The active electronic device 103 is powered by a contactless power source 120, such as a wireless power source. The contactless power source 120 may include inductive, capacitive, or magneto-dynamic contactless power transfer or any other suitable contactless power transfer. Referring to FIGS. 4 and 5, the contactless power source 120 includes a power source transmitter 122 and a power source receiver 124. The power source transmitter 122 is associated with the stationary platform 48 upon which the yoke assembly rotates. In the illustrated embodiment, the power source transmitter 122 is a relatively flat plate which is associated with a surface 126 of the platform 48 facing the yoke 50. For example, the power source transmitter 122 may be located on or embedded in surface 126. The power source receiver 124 is associated with a rotating component of the centrifuge 16, such as the rotating yoke 50. In the illustrated embodiment, the power source receiver 124 is a relatively flat plate that is associated with a surface 128 of the rotating yoke 50 facing the stationary platform 48. For example, the power source receiver 124 may be located on or embedded in surface 128.

The active electronic device 103 is powered by the contactless power source 120. In the illustrated embodiment, the active electronic device 103 is operatively connected to the power source receiver 124 by one or more wires 130. In the embodiment shown, the wire(s) 130 are shown in broken-line to indicate that they are located or run within the structures of the rotating yoke 50. In other embodiments, the wire(s) 130 may run along the outer surfaces of the rotating yoke 50.

During centrifugation, the rotating yoke 50 rotates relative to the stationary platform 48. The power source transmitter 122 on the stationary platform transmits energy to the power source receiver 124. The power source receiver 124 powers the active electronic device 103, which may be sensor. In one embodiment, the active electronic device may be electric drive 72.

The active electronic device 103 may exchange data wirelessly with another device 105 that is not located on the rotating component of the centrifuge. For example, the other device 105 is not located on or associated with yoke 50. The other device 105 may be for example the controller 32 or in the controller 32 (FIG. 1) which not located on the rotating component. The active electronic device 103 may have a wireless data exchange device 107 that exchanges (sends and/or receives) data a separate data exchange device 109 of the other device 105. The data may be exchanged via one or more of Bluetooth, Wi-Fi, near field communication or any other suitable wireless peer-to-peer communication. Additionally, the electronic device 103 and the other device 105 also may convert analog data to digital data for wireless transmission.

The combination of the use of the contactless power source 120 and the wireless data exchange results in the ability to use an active electronic device 103 on the rotating component of the centrifuge with little or no mechanical connections. This configuration achieves greater reliability of the active electronic device and less mechanical failures.

Furthermore, this combination may be employed in other fields outside of the blood separation. For example, other fields and structures that include an active electronic device on a rotating component.

Figure 6:
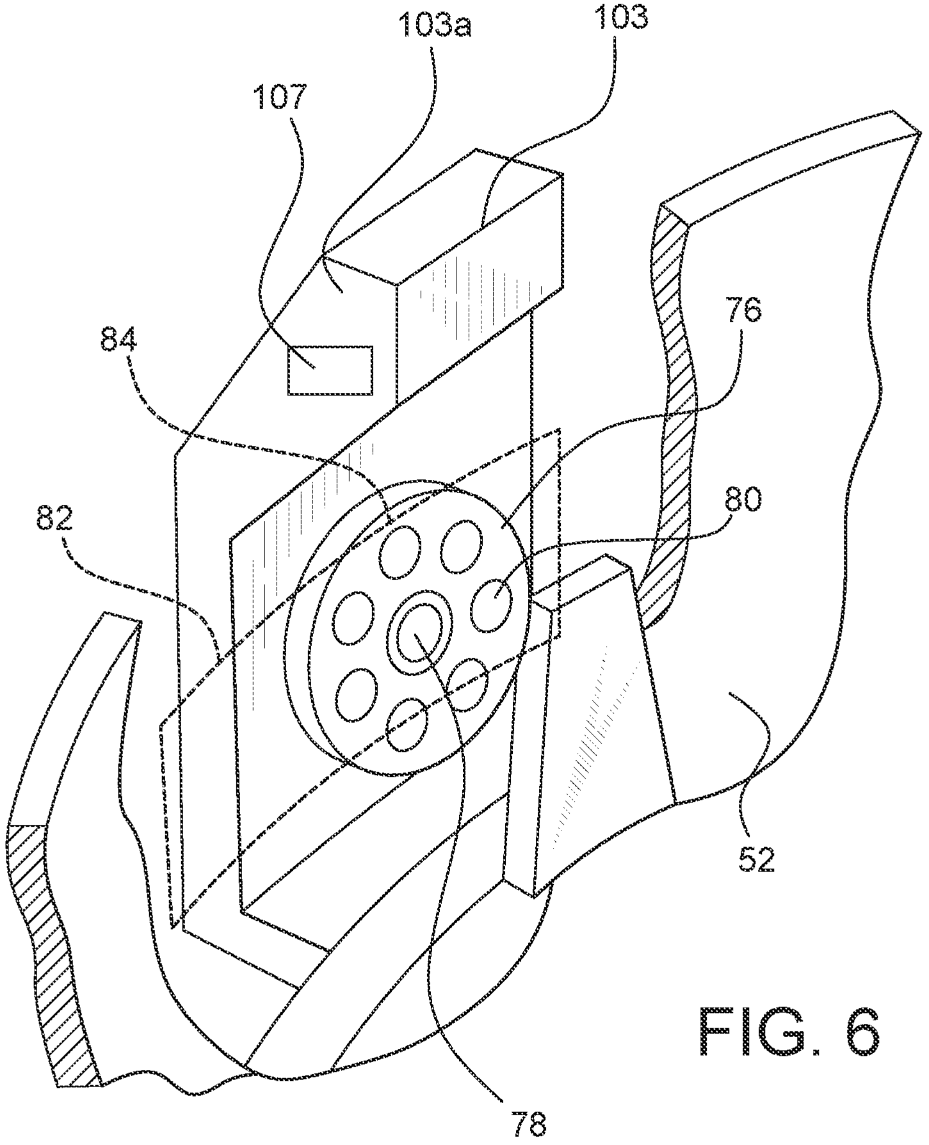
FIG. 6 is an example of an active device on the rotating component of the centrifuge assembly.

As discussed above, the active electronic device may be any suitable device, such as a sensor or detector that provides information regarding the characteristics of the blood or the operation of the centrifuge. FIG. 6 illustrates an exemplary active electronic device 103. The active electronic device 103 may be an optical sensor 103*a* that senses the optical characteristics of fluid during the separation process. The sensor 103*a* may be carried by the cross member 62 (FIG. 4) of the rotating yoke 50. The sensor 103*a* includes a light source 76, which emits light that is absorbed by the fluid, for example red blood cells. In the illustrated embodiment, the light source 76 includes a circular array of red light emitting diodes 84. Of course, other wavelengths absorbed by RBC, like green or infrared, could be used.

The sensor 103*a* also includes a light detector 78, which is mounted adjacent to the light source 76. In the illustrated and preferred embodiment, the light detector 78 comprises a PIN diode detector, which is located generally in the geometric center of the circular array of light emitting diodes 84.

The yoke 50 and sensor 103*a* rotate relative to the platform 48. Furthermore, the centrifuge chamber assembly 52 rotates relative to the sensor 103*a*. The light source 76 directs light onto the chamber assembly 52. In the illustrated embodiment, the chamber assembly 52 is transparent to the light emitted by the source 76 in the region 86. In the illustrated embodiment, the region 86 comprises a window cut out in the chamber assembly 52. The remainder of the chamber assembly 52 that lies in the path of the sensor 103*a* comprises a light absorbing material.

The light from the source 76 will thereby pass through the transparent region 86 of the chamber assembly 52 every time the rotating chamber assembly 52 and sensor 103*a* align. The light is reflected back to toward the sensor, where it is sensed by the detector 78.

As the transparent interface region 86 of the chamber assembly 52 comes into alignment with the sensor 103*a*, the detector 78 will first sense light reflected through a plasma layer. Eventually, a red blood cell layer will enter the optical path of the sensor 103*a*. The red blood cell layer absorbs light from the source 76 and thereby reduces the previously sensed intensity of the reflected light. The intensity of the reflected light sensed by the detector 78 represents the amount of light from the source 76 that is not absorbed by the red blood cell layer.

The sensor (active device) may exchange data wirelessly with another device that is not located on the rotating component of the centrifuge. The other device may be for example the controller 32 which not located on the rotating component. For example, the sensor may have a wireless data exchange member that exchanges (sends and/or receives) data a separate data exchange member of a device not physically associated with the rotating component of the centrifuge that includes the sensor. Data from the sensor 103*a* may be wirelessly transmitted to the other device 105. For example, data from sensor 103*a* may be sent to the controller 32, which then adjusts the centrifuge based on the data. Furthermore, analog data from the sensor 103*a* may be digitized before being wirelessly transmitted by wireless exchange device 107 to the controller 32.

ASPECTS

Aspect 1. A centrifuge assembly for processing blood and components, comprising: a base; a rotating component that rotates relative to the base; a contactless power source including a power source transmitter associated with the base and a power source receiver associated with the rotating component, wherein the power source transmitter wirelessly transmits power to the power source receiver; and an active electronic device associated with the rotating component and operatively connected to the power source receiver, wherein the power source receiver provides power to the active electronic device.

Aspect 2. The centrifuge assembly of Aspect 1, wherein the active electronic device exchanges data with another device that is not located on the rotating component.

Aspect 3. The centrifuge assembly of Aspect 2, wherein the active electronic device wirelessly exchanges data with the another device not located on the rotating component.

Aspect 4. The centrifuge assembly of Aspect 3, wherein wireless exchange of data is via one or more of Bluetooth, Wi-Fi, and near field communication.

Aspect 5. The centrifuge assembly of any one of Aspects 3 and 4, wherein the active electronic device includes a first wireless data exchange device and the another device not located on the rotating component includes a second wireless data exchange device, wherein the first and second wireless data exchange devices exchange data with one another.

Aspect 6. The centrifuge assembly of any one of Aspects 2-5, wherein the another device not located on the rotating component comprises a controller.

Aspect 7. The centrifuge assembly of any one of Aspects 1-6, wherein the active electronic device comprises a sensor.

Aspect 8. The centrifuge assembly of Aspect 7, wherein the sensor senses one or more characteristics of blood and/or blood components.

Aspect 9. The centrifuge assembly of Aspect 8, wherein the sensor comprises an optical sensor.

Aspect 10. The centrifuge assembly of Aspect 7, wherein the sensor senses one or more characteristics of the centrifuge assembly.

Aspect 11. The centrifuge assembly of any one of Aspects 1-6, wherein the active electronic device comprises one or more of a blood component detector, an interface detector, pressure sensor, temperature sensor, hemolysis sensor, weight scale and camera.

Aspect 12. A method of processing blood and/or components with a centrifuge assembly, comprising: flowing blood and/or blood components to a rotating component of a centrifuge assembly; rotating the rotating component of the centrifuge assembly relative to a base; and powering an active electronic device associated with the rotating component with a contactless power source.

Aspect 13. The method of Aspect 12, wherein the contactless power source includes a power source transmitter and a power source receiver, wherein the power source transmitter is associated with the base and the power source receiver is associated with the rotating component; and wherein the power source receiver provides power to the active electronic device.

Aspect 14. The method of any one of Aspects 12 and 13, further including exchanging data between the active electronic device and another device not located on the rotating component.

Aspect 15. The method of Aspect 14, wherein the exchanging of data between the active electronic device and the another device comprises wirelessly exchanging data.

Aspect 16. The method of Aspect 15, wherein wireless exchange of data is via one or more of Bluetooth, Wi-Fi, and near field communication.

Aspect 17. The method of any one of Aspects 15 and 16, wherein the active electronic device includes a first wireless data exchange device and the another device not located on the rotating component includes a second wireless data exchange device, wherein the first and second wireless data exchange devices exchange data with one another.

Aspect 18. The method of any one of Aspects 14-17, wherein the another device not located on the rotating component comprises a controller.

Aspect 19. The method of any one of Aspects 12-18, wherein the active electronic device comprises a sensor.

Aspect 20. The method of Aspect 19, wherein the sensor senses one or more characteristics of blood and/or blood components.

Aspect 21. The method of any one of Aspects 19 and 20, wherein the sensor comprises an optical sensor.

Aspect 22. The method of Aspect 19, wherein the sensor senses one or more characteristics of the centrifuge assembly.

Aspect 23. The method of any one of Aspects 12-18, wherein the active electronic device comprises one or more of a blood component detector, an interface detector, pressure sensor, temperature sensor, hemolysis sensor, weight scale, and camera.

The invention claimed is:

1. A centrifuge assembly for processing blood and components, comprising:

- a stationary platform;
- a rotating component that rotates relative to the stationary platform, the rotating component having a rotating component base;
- a drive shaft attached to the rotating component base;
- a motor housed in the stationary platform, the motor spinning the drive shaft relative to the stationary platform, thereby rotating the rotating component relative to the stationary platform;
- a contactless power source including a power source transmitter and a power source receiver, the power source transmitter configured to wirelessly transmit power to the power source receiver, the power source transmitter being directly located on or embedded in a surface of the stationary platform facing the rotating component and the power source receiver being directly located on or embedded in a surface of the rotating component facing the stationary platform; and
- an active electronic device associated with the rotating component and operatively connected to the power source receiver, the power source receiver configured to provide power to the active electronic device.

2. The centrifuge assembly of claim 1, wherein the active electronic device exchanges data with another device that is not located on the rotating component.

3. The centrifuge assembly of claim 2, wherein the active electronic device wirelessly exchanges data with the another device not located on the rotating component.

4. The centrifuge assembly of claim 3, wherein wireless exchange of data is via one or more of Bluetooth, Wi-Fi, and near field communication.

5. The centrifuge assembly of claim 3, wherein the active electronic device includes a first wireless data exchange device and the another device not located on the rotating component includes a second wireless data exchange device, wherein the first and second wireless data exchange devices exchange data with one another.

6. The centrifuge assembly of claim 2, wherein the another device not located on the rotating component comprises a controller.

7. The centrifuge assembly of claim 1, wherein the active electronic device comprises a sensor.

8. The centrifuge assembly of claim 7, wherein the sensor senses one or more characteristics of blood and/or blood components.

9. The centrifuge assembly of claim 8, wherein the sensor comprises an optical sensor.

10. The centrifuge assembly of claim 7, wherein the sensor senses one or more characteristics of the centrifuge assembly.

11. The centrifuge assembly of claim 1, wherein the active electronic device comprises one or more of a blood component detector, an interface detector, pressure sensor, temperature sensor, hemolysis sensor, weight scale and camera.

12. A method of processing blood and/or components with a centrifuge assembly that comprises a stationary platform, a rotating component that rotates relative to the stationary platform, the rotating component having a rotating component base, a drive shaft attached to the rotating component base, a motor housed in the stationary platform, the motor spinning the drive shaft relative to the stationary platform, thereby rotating the rotating component relative to the stationary platform, a contactless power source including a power source transmitter and a power source receiver, wherein the power source transmitter wirelessly transmits power to the power source receiver, the power source transmitter being directly located on or embedded in a surface of the stationary platform facing the rotating component and the power source receiver being directly located on or embedded in a surface of the rotating component facing the stationary platform, and an active electronic device associated with the rotating component and operatively connected to the power source receiver, wherein the power source receiver provides power to the active electronic device, the method comprising:

- flowing blood and/or blood components to the rotating component of the centrifuge assembly;
- rotating the rotating component of the centrifuge assembly relative to the stationary platform; and
- powering the active electronic device associated with the rotating component with the contactless power source.

13. The method of claim 12, further including exchanging data between the active electronic device and another device not located on the rotating component.

14. The method of claim 13, wherein the exchanging of data between the active electronic device and the another device comprises wirelessly exchanging data.

15. The method of claim 14, wherein wireless exchange of data is via one or more of Bluetooth, Wi-Fi, and near field communication.

16. The method of claim 14, wherein the active electronic device includes a first wireless data exchange device and the another device not located on the rotating component includes a second wireless data exchange device, wherein the first and second wireless data exchange devices exchange data with one another.

17. The method of claim 13, wherein the another device not located on the rotating component comprises a controller.

18. The method of claim 17, wherein the active electronic device comprises a sensor.

19. The method of claim 18, wherein the sensor senses one or more characteristics of blood and/or blood components.

* * * * *